(12) United States Patent
Schubert et al.

(10) Patent No.: US 8,957,009 B2
(45) Date of Patent: *Feb. 17, 2015

(54) LINEAR POLYDIMETHYLSILOXANE-POLYETHER COPOLYMERS HAVING AMINO AND/OR QUATERNARY AMMONIUM GROUPS AND USE THEREOF

(75) Inventors: Frank Schubert, Neukirchen-Vluyn (DE); Wilfried Knott, Essen (DE); Michael Ferenz, Essen (DE); Klaus-Dieter Klein, Mülheim an der Ruhr (DE); Tobias Maurer, Velbert (DE); Ralph Scheuermann, Essen (DE); Bernard William Kluesener, Harrison, OH (US); Rajan Keshav Panandiker, West Chester, OH (US)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/520,091

(22) PCT Filed: Dec. 29, 2010

(86) PCT No.: PCT/EP2010/070838
§ 371 (c)(1),
(2), (4) Date: Jun. 29, 2012

(87) PCT Pub. No.: WO2011/091933
PCT Pub. Date: Aug. 4, 2011

(65) Prior Publication Data
US 2012/0308494 A1 Dec. 6, 2012

(30) Foreign Application Priority Data
Jan. 29, 2010 (DE) .......................... 10 2010 001 350

(51) Int. Cl.
| C08G 77/388 | (2006.01) |
| C08G 77/46 | (2006.01) |
| A61K 8/898 | (2006.01) |
| A61Q 19/00 | (2006.01) |
| D06M 15/643 | (2006.01) |
| D06M 15/647 | (2006.01) |
| A61Q 5/00 | (2006.01) |

(52) U.S. Cl.
CPC ................ *C08G 77/46* (2013.01); *A61K 8/898* (2013.01); *A61Q 19/00* (2013.01); *C08G 77/388* (2013.01); *D06M 15/6436* (2013.01); *D06M 15/647* (2013.01); *A61Q 5/00* (2013.01)
USPC ............................ 510/466; 525/474; 252/8.63

(58) Field of Classification Search
None
See application file for complete search history.

(56) References Cited

U.S. PATENT DOCUMENTS

| 3,389,160 A | 6/1968 | Reid et al. |
| 4,081,384 A | 3/1978 | Pracht |
| 4,133,779 A | 1/1979 | Hellyer et al. |
| 4,228,042 A | 10/1980 | Letton |
| 4,234,627 A | 11/1980 | Schilling |
| 4,239,660 A | 12/1980 | Kingry |
| 4,260,529 A | 4/1981 | Letton |
| 4,483,779 A | 11/1984 | Llenado et al. |
| 4,483,780 A | 11/1984 | Llenado |
| 4,514,461 A | 4/1985 | Woo |
| 4,565,647 A | 1/1986 | Llenado |
| 4,681,704 A | 7/1987 | Bernardino et al. |
| RE32,713 E | 7/1988 | Woo |
| 4,767,547 A | 8/1988 | Straathof et al. |
| 4,882,220 A | 11/1989 | Ono et al. |
| 4,891,166 A | 1/1990 | Schaefer et al. |
| 4,895,964 A | 1/1990 | Margida et al. |
| 4,917,920 A | 4/1990 | Ono et al. |
| 4,981,239 A | 1/1991 | Cappel et al. |
| 5,137,646 A | 8/1992 | Schmidt et al. |
| 5,143,288 A | 9/1992 | Kohler et al. |
| 5,145,842 A | 9/1992 | Driedger et al. |
| 5,306,434 A | 4/1994 | Schueller et al. |
| 5,332,528 A | 7/1994 | Pan et al. |
| 5,344,949 A | 9/1994 | Koerner et al. |
| 5,371,161 A | 12/1994 | Knott |
| 5,430,166 A | 7/1995 | Klein et al. |
| 5,430,167 A | 7/1995 | Klein et al. |
| 5,455,367 A | 10/1995 | Klein et al. |
| 5,460,736 A | 10/1995 | Trinh et al. |
| 5,470,492 A | 11/1995 | Childs et al. |
| 5,474,690 A | 12/1995 | Wahl et al. |
| 5,475,127 A | 12/1995 | Klein et al. |

(Continued)

FOREIGN PATENT DOCUMENTS

| DE | 1493384 | 1/1969 |
| DE | 3719086 | 10/1988 |

(Continued)

OTHER PUBLICATIONS

Japanese Office Action in JP Patent Application No. 2012-550352, Mailing No. 095652, mailed Feb. 18, 2014 (with English translation thereof).

*Primary Examiner* — Kevin S Orwig
*Assistant Examiner* — Dominic Lazaro
(74) *Attorney, Agent, or Firm* — Frommer Lawrence & Haug LLP

(57) ABSTRACT

Linear polydimethylsiloxane-polyether copolymers with amino and/or quaternary ammonium groups, obtainable by the reaction of organopolysiloxanes functionalized with secondary aminoalkyl groups with the reaction products formed from compounds containing epoxy groups and amines, the use thereof and process for preparation thereof.

2 Claims, No Drawings

(56) References Cited

U.S. PATENT DOCUMENTS

| | | | |
|---|---|---|---|
| 5,476,599 A | 12/1995 | Rusche et al. | |
| 5,486,634 A * | 1/1996 | Hahn et al. | 556/425 |
| 5,545,340 A | 8/1996 | Wahl et al. | |
| 5,545,350 A | 8/1996 | Baker et al. | |
| 5,562,849 A | 10/1996 | Wahl et al. | |
| 5,574,179 A | 11/1996 | Wahl et al. | |
| 5,576,282 A | 11/1996 | Miracle et al. | |
| 5,783,544 A | 7/1998 | Trinh et al. | |
| 5,798,107 A | 8/1998 | Vogel et al. | |
| 5,807,956 A | 9/1998 | Czech et al. | |
| 5,856,548 A | 1/1999 | Drose et al. | |
| 5,883,069 A | 3/1999 | Childs et al. | |
| 5,929,026 A | 7/1999 | Childs et al. | |
| 5,934,579 A | 8/1999 | Hiersche et al. | |
| 5,939,060 A | 8/1999 | Trinh et al. | |
| 5,980,931 A | 11/1999 | Fowler et al. | |
| 5,981,681 A | 11/1999 | Czech et al. | |
| 5,981,812 A | 11/1999 | Eufinger et al. | |
| 6,001,343 A | 12/1999 | Trinh et al. | |
| 6,004,922 A | 12/1999 | Watson et al. | |
| 6,008,181 A | 12/1999 | Cripe et al. | |
| 6,020,303 A | 2/2000 | Cripe et al. | |
| 6,022,844 A | 2/2000 | Baillely et al. | |
| 6,060,443 A | 5/2000 | Cripe et al. | |
| 6,077,318 A | 6/2000 | Trinh et al. | |
| 6,093,856 A | 7/2000 | Cripe et al. | |
| 6,121,165 A | 9/2000 | Mackey et al. | |
| 6,123,738 A * | 9/2000 | Childers et al. | 8/102 |
| 6,136,769 A | 10/2000 | Asano et al. | |
| 6,153,577 A | 11/2000 | Cripe et al. | |
| 6,200,949 B1 | 3/2001 | Reijmer et al. | |
| 6,207,141 B1 | 3/2001 | Pyles et al. | |
| 6,221,825 B1 | 4/2001 | Williams, Jr. et al. | |
| 6,255,511 B1 | 7/2001 | Klein et al. | |
| 6,274,540 B1 | 8/2001 | Scheibel et al. | |
| 6,279,834 B1 | 8/2001 | Fox et al. | |
| 6,291,622 B1 | 9/2001 | Drose et al. | |
| 6,306,812 B1 | 10/2001 | Perkins et al. | |
| 6,307,082 B1 | 10/2001 | Klein et al. | |
| 6,326,348 B1 | 12/2001 | Vinson et al. | |
| 6,361,752 B1 | 3/2002 | Demarest et al. | |
| 6,475,568 B1 | 11/2002 | Czech | |
| 6,482,358 B1 | 11/2002 | Kelsch et al. | |
| 6,482,994 B2 | 11/2002 | Scheper et al. | |
| 6,489,498 B2 | 12/2002 | Klein et al. | |
| 6,491,840 B1 | 12/2002 | Frankenbach et al. | |
| 6,492,322 B1 | 12/2002 | Cooper et al. | |
| 6,495,058 B1 | 12/2002 | Frankenbach et al. | |
| 6,495,498 B2 | 12/2002 | Niemiec et al. | |
| 6,551,986 B1 | 4/2003 | Littig et al. | |
| 6,573,233 B1 | 6/2003 | Altmann et al. | |
| 6,592,813 B1 | 7/2003 | Fox et al. | |
| 6,593,285 B1 | 7/2003 | Scheibel et al. | |
| 6,642,200 B1 | 11/2003 | Zhang et al. | |
| 6,645,479 B1 | 11/2003 | Shefer et al. | |
| 6,696,053 B1 | 2/2004 | Ma et al. | |
| 6,733,538 B1 | 5/2004 | Panandiker et al. | |
| 6,779,740 B1 | 8/2004 | Lentsch et al. | |
| 6,790,408 B2 | 9/2004 | Whitby et al. | |
| 6,844,309 B1 | 1/2005 | Sivik et al. | |
| 6,858,663 B2 | 2/2005 | Knott et al. | |
| 6,883,723 B2 | 4/2005 | Griese et al. | |
| 6,899,281 B1 | 5/2005 | Griese et al. | |
| 6,908,041 B2 | 6/2005 | Griese et al. | |
| 6,910,640 B2 | 6/2005 | Griese et al. | |
| 6,910,641 B2 | 6/2005 | Griese et al. | |
| 6,949,498 B2 | 9/2005 | Murphy et al. | |
| 6,956,017 B1 | 10/2005 | Catalan et al. | |
| 7,018,458 B2 | 3/2006 | Knott et al. | |
| 7,055,761 B2 | 6/2006 | Griese et al. | |
| 7,087,572 B2 | 8/2006 | Hubig et al. | |
| 7,093,772 B2 | 8/2006 | Griese et al. | |
| 7,119,057 B2 | 10/2006 | Popplewell et al. | |
| 7,125,585 B2 | 10/2006 | Dudzik et al. | |
| 7,135,451 B2 | 11/2006 | Corona, III et al. | |
| 7,157,541 B2 | 1/2007 | Knott et al. | |
| 7,186,680 B2 | 3/2007 | Caswell et al. | |
| 7,196,153 B2 | 3/2007 | Burkhart et al. | |
| 7,223,361 B2 | 5/2007 | Kvietok et al. | |
| 7,250,393 B2 | 7/2007 | Lentsch et al. | |
| 7,262,159 B2 | 8/2007 | Nguyen et al. | |
| 7,309,026 B2 | 12/2007 | Griese et al. | |
| 7,381,697 B2 | 6/2008 | Lentsch et al. | |
| 7,452,855 B2 | 11/2008 | Hubig et al. | |
| 7,456,145 B2 | 11/2008 | Lentsch et al. | |
| 7,598,334 B2 | 10/2009 | Ferenz | |
| 7,605,284 B2 | 10/2009 | Brueckner et al. | |
| 7,612,158 B2 | 11/2009 | Burkhart et al. | |
| 7,612,159 B2 | 11/2009 | Burkhart et al. | |
| 7,619,035 B2 | 11/2009 | Henning et al. | |
| 7,625,857 B2 | 12/2009 | Ward et al. | |
| 7,635,581 B2 | 12/2009 | Ferenz et al. | |
| 7,645,848 B2 | 1/2010 | Knott et al. | |
| 7,727,599 B2 | 6/2010 | Doehler et al. | |
| 7,754,778 B2 | 7/2010 | Knott et al. | |
| 7,776,989 B2 | 8/2010 | Ferenz et al. | |
| 7,799,752 B2 | 9/2010 | Ness et al. | |
| 7,825,205 B2 | 11/2010 | Knott et al. | |
| 7,825,206 B2 | 11/2010 | Neumann et al. | |
| 7,825,207 B2 | 11/2010 | Ferenz et al. | |
| 7,825,209 B2 | 11/2010 | Knott et al. | |
| 7,834,122 B2 | 11/2010 | Ferenz et al. | |
| 7,838,603 B2 | 11/2010 | Schwab et al. | |
| 7,855,265 B2 | 12/2010 | Thum et al. | |
| 7,893,128 B2 | 2/2011 | Busch et al. | |
| 7,964,694 B2 | 6/2011 | Ferenz et al. | |
| 8,030,366 B2 | 10/2011 | Ferenz et al. | |
| 8,138,294 B2 | 3/2012 | Henning et al. | |
| 8,158,572 B2 * | 4/2012 | Schubert et al. | 510/466 |
| 8,172,936 B2 | 5/2012 | Herrwerth et al. | |
| 8,198,473 B2 | 6/2012 | Ferenz et al. | |
| 2002/0066798 A1 | 6/2002 | Laudamiel-Pellet et al. | |
| 2002/0161158 A1 | 10/2002 | Burkhart et al. | |
| 2003/0060390 A1 | 3/2003 | Demeyere et al. | |
| 2003/0126282 A1 | 7/2003 | Sarlcar et al. | |
| 2003/0158344 A1 | 8/2003 | Rodriques et al. | |
| 2003/0165692 A1 | 9/2003 | Koch et al. | |
| 2003/0195133 A1 | 10/2003 | Shefer et al. | |
| 2003/0203829 A1 | 10/2003 | Shefer | |
| 2003/0215417 A1 | 11/2003 | Uchiyama | |
| 2003/0216488 A1 | 11/2003 | Uchiyama | |
| 2004/0071742 A1 | 4/2004 | Popplewell | |
| 2004/0071746 A1 | 4/2004 | Popplewell | |
| 2004/0072719 A1 | 4/2004 | Bennett | |
| 2004/0072720 A1 | 4/2004 | Brain | |
| 2004/0087477 A1 | 5/2004 | Ness | |
| 2004/0106536 A1 | 6/2004 | Mane | |
| 2004/0204431 A1 | 10/2004 | Corona | |
| 2004/0225099 A1 * | 11/2004 | Hohberg et al. | 528/25 |
| 2006/0155090 A1 | 7/2006 | Ferenz | |
| 2006/0252668 A1 | 11/2006 | Frankenbach | |
| 2006/0275238 A1 | 12/2006 | Blasko-Begoihn et al. | |
| 2007/0059539 A1 | 3/2007 | Doehler et al. | |
| 2007/0128143 A1 | 6/2007 | Gruening et al. | |
| 2007/0197678 A1 | 8/2007 | Cavaleiro et al. | |
| 2007/0281877 A1 | 12/2007 | Nguyen | |
| 2008/0004357 A1 | 1/2008 | Meyer et al. | |
| 2008/0187702 A1 | 8/2008 | Ferenz et al. | |
| 2008/0191370 A1 | 8/2008 | Pankhurst | |
| 2008/0227923 A1 | 9/2008 | Klein et al. | |
| 2008/0242584 A1 | 10/2008 | Wahl | |
| 2008/0305982 A1 | 12/2008 | Smets | |
| 2009/0137751 A1 | 5/2009 | Knott et al. | |
| 2009/0137752 A1 | 5/2009 | Knott et al. | |
| 2009/0189986 A1 | 7/2009 | Scheuermann et al. | |
| 2009/0247449 A1 | 10/2009 | Burdis | |
| 2010/0022435 A1 | 1/2010 | Henning et al. | |
| 2010/0034765 A1 | 2/2010 | Herrwerth et al. | |
| 2010/0036011 A1 | 2/2010 | de Gans et al. | |
| 2010/0041629 A1 | 2/2010 | Giessler-Blank et al. | |
| 2010/0041910 A1 | 2/2010 | Schubert et al. | |
| 2010/0055760 A1 | 3/2010 | Thum et al. | |
| 2010/0071849 A1 | 3/2010 | Knott et al. | |
| 2010/0081763 A1 | 4/2010 | Meyer et al. | |

(56) References Cited

U.S. PATENT DOCUMENTS

| | | |
|---|---|---|
| 2010/0081781 A1 | 4/2010 | Schubert et al. |
| 2010/0105843 A1 | 4/2010 | Knott et al. |
| 2010/0113633 A1 | 5/2010 | Henning et al. |
| 2010/0168367 A1 | 7/2010 | Schubert et al. |
| 2010/0184913 A1 | 7/2010 | Ebbrecht et al. |
| 2010/0210445 A1 | 8/2010 | Von Rymon Lipinski et al. |
| 2010/0248325 A1 | 9/2010 | Eckstein et al. |
| 2010/0249339 A1 | 9/2010 | Henning et al. |
| 2010/0266518 A1 | 10/2010 | Springer et al. |
| 2010/0266651 A1 | 10/2010 | Czech et al. |
| 2010/0292357 A1 | 11/2010 | Knott et al. |
| 2010/0298455 A1 | 11/2010 | Henning et al. |
| 2011/0021096 A1 | 1/2011 | Falk |
| 2011/0021693 A1 | 1/2011 | Henning et al. |
| 2011/0034576 A1 | 2/2011 | Henning et al. |
| 2011/0042004 A1 | 2/2011 | Schubert et al. |
| 2011/0046305 A1 | 2/2011 | Schubert et al. |
| 2011/0070175 A1 | 3/2011 | Herrwerth et al. |
| 2011/0091399 A1 | 4/2011 | Meyer et al. |
| 2011/0172373 A1 | 7/2011 | Knott et al. |
| 2011/0230619 A1 | 9/2011 | Kuppert et al. |
| 2011/0230633 A1 | 9/2011 | Ferenz et al. |
| 2011/0245412 A1 | 10/2011 | Schubert et al. |
| 2011/0251070 A1 | 10/2011 | Poffenberger et al. |
| 2011/0281973 A1 | 11/2011 | Schubert et al. |
| 2011/0301254 A1 | 12/2011 | Knott et al. |
| 2012/0010302 A1 | 1/2012 | Hartung et al. |
| 2012/0028022 A1 | 2/2012 | Brugger et al. |
| 2012/0029090 A1 | 2/2012 | Brugger et al. |
| 2012/0037036 A1 | 2/2012 | Veit et al. |

FOREIGN PATENT DOCUMENTS

| | | |
|---|---|---|
| EP | 0017122 | 10/1980 |
| EP | 0294642 | 5/1988 |
| EP | 0399108 A1 * | 5/1989 |
| EP | 0530974 | 3/1993 |
| EP | 0617607 | 10/1994 |
| EP | 1080714 | 3/2001 |
| JP | S46-28236 | 8/1971 |
| JP | H 11504980 | 5/1999 |
| JP | 2000-191456 | 7/2000 |
| JP | 2004-331977 | 11/2004 |
| WO | WO 94/08556 | 4/1994 |
| WO | WO 97/32917 | 9/1997 |
| WO | WO 98/35002 | 8/1998 |
| WO | WO 98/35003 | 8/1998 |
| WO | WO 98/35004 | 8/1998 |
| WO | WO 98/35005 | 8/1998 |
| WO | WO 98/35006 | 8/1998 |
| WO | WO 99/05244 | 2/1999 |
| WO | WO 00/47708 | 8/2000 |
| WO | WO 01/82879 | 11/2001 |
| WO | WO 02/092904 | 11/2002 |
| WO | WO 2008/138363 | 11/2008 |

* cited by examiner

LINEAR POLYDIMETHYLSILOXANE-POLYETHER COPOLYMERS HAVING AMINO AND/OR QUATERNARY AMMONIUM GROUPS AND USE THEREOF

The present application claims priority from PCT Patent Application No. PCT/EP2010/070838 filed on Dec. 29, 2010, which claims priority from German Patent Application No. DE 10 2010 001 350.1 filed on Jan. 29, 2010, the disclosures of which are incorporated herein by reference in their entirety.

BACKGROUND OF THE INVENTION

1. Field of the Invention

The invention relates to novel linear polydimethylsiloxane-polyether copolymers with amino and/or quaternary ammonium groups. It further relates to the use of these polymers as softeners for fabrics, for example wovens, especially textile wovens, tissue, nonwovens and/or fibres of natural and/or synthetic raw materials and/or leather, hair or hide, and to the use thereof in cosmetic applications, for example in haircare, skincare and personal hygiene.

It is noted that citation or identification of any document in this application is not an admission that such document is available as prior art to the present invention.

Softeners for fabrics, for example wovens, textile wovens, knits, nonwovens and/or fibres of natural and/or synthetic raw materials, are substances which impart a soft supple hand to the materials mentioned. Particularly suitable softeners are polysiloxanes with quaternary ammonium groups. By virtue of electrostatic attractive forces, the ionic groups anchor the siloxane to the fibre. In this way, friction is reduced and the desired softener effect is achieved. When the siloxane is applied in the form of microemulsions, it can additionally penetrate into the fibre and imparts inner softness and fullness thereto.

There are specific formulations for the care of damaged hair, such as hair rinses, hair repair treatments, shampoos, leave-on conditioners, etc., which in particular improve the combability, hand and shine of damaged hair. Such conventional haircare compositions comprise principally cationic surfactants based on alkylammonium, polymers, waxes or oils, or silicone oils. The efficacy of these compounds can be attributed to hydrophobization of the hair surface, among other causes.

For all these compositions, a good care action (conditioning) of the hair is achieved, but the appearance, especially the shine of the hair, is not improved by the care products, but in some cases even worsened.

There is therefore a need for versatile active ingredients for personal hygiene and care products, such as shampoos, hair treatment compositions and hair aftertreatment compositions, which, in addition to cleaning action, improve the care of the hair and simultaneously impart good shine, which protect the hair from damage to the hair structure and which minimize structural damage already caused to the hair, resulting from environmental influences and from shaping and colouring treatments.

Polysiloxanes with quaternary ammonium groups are known as additives for haircare. For example, DE 14 93 384, EP 0 017 122 and U.S. Pat. No. 4,895,964 describe structures in which siloxanes are modified with pendant ammonium groups distributed randomly over the polymer. These compounds have the disadvantage that they do not possess any marked silicone character, and good efficacy is not observed.

A more marked silicone character is possessed by cationic polysiloxanes as described in DE 37 19 086 and EP 0 294 642. In the structures described in DE 37 19 086 and in EP 0 294 642, the quaternary functions are bonded terminally to the polysiloxane. Such compounds offer advantages with regard to the action thereof as conditioners, both for hair and textiles and for hard surfaces. The use of such compounds in cosmetic formulations is described, for example, in EP 0 530 974, EP 617 607, EP 1 080 714, WO 2001/082879 and U.S. Pat. No. 6,207,141.

However, the structures described there possess only two cationic groups. Owing to the relatively minor electrostatic interaction of the polysiloxanes provided with two charge centres present at their termini, the affinity thereof for particular surfaces and, as a consequence thereof, also the substantivity thereof, i.e. the tendency thereof to become anchored permanently thereto, is comparatively low.

Polysiloxanes with pendant quaternary ammonium groups distributed randomly over the polymer and the use thereof as textile softeners are described, for example, in DE-B 14 93 384. These compounds have the disadvantage that they do not possess marked silicone character, and good efficacy as a textile softener is not observed.

A significantly more marked silicone character is possessed, in contrast, by cationic silicones as described in EP 0 294 642. EP 0 294 642 describes structures in which the quaternary functions are bonded terminally to a siloxane segment. When a textile is treated with such compounds, it receives good softness, but the siloxane is removable again easily from the corresponding textile owing to its low substantivity, for example by washing operations. In contrast to the domestic fabric softener, it is, however, desirable for industrial textile end finishing that the siloxane remains on the textile even after the wash and the softness is thus not lost.

Addressing the aspect of increased hydrophilicity, U.S. Pat. No. 5,807,956 and U.S. Pat. No. 5,981,681 claim non-hydrolysable block copolymers of the $(AB)_n A$ type with alternating units consisting of polysiloxane and amino-polyalkylene oxide, and a route for preparation thereof. For instance, noble metal-catalysed hydrosilylation produces SiC linkages of $\alpha,\omega$-dihydrogenpolydimethylsiloxanes with olefins bearing epoxy groups, and the epoxy-terminated siloxanes thus obtained are reacted with amino-terminated polyalkylene oxides. Another alternative is the hydrosilylating linkage of $\alpha,\omega$-dihydrogenpolydimethylsiloxanes with epoxy-terminated allyl polyethers and the subsequent reaction of the epoxy-functionalized siloxanes thus obtained with diamines.

The teaching of WO 02/092904 relates to compositions consisting of nonhydrolysable block-type copolymers which do not possess an $(AB)_n$ structure, and which are obtained by the reaction between polydimethylsiloxanes A having epoxy groups and polyalkylene oxides B bearing epoxy termini in the presence of primary amines and/or mixtures consisting of primary and secondary amines. The presence of different epoxy substrates leads, in the presence of the aminic reactants, to a virtually uncontrollable, self-organized polyaddition process which, beyond an unachievable strict $(A(amine)B)_n$ structure, leads to a copolymer which, in varying population, has both homogeneously distributed (A(amine)A) and (B(amine)B) and heterogeneously distributed (A(amine)B) diades each linked aminically. Owing to the siloxane reactants provided with epoxy functions, the copolymer structures thus obtained are capable of linkage of the particular siloxanyl units via an ether function to the aminoorganic radicals of the copolymer. With the option of further elaboration for neutralization and/or quaternization, the substantivity for textile or fibrous surfaces can be adjusted. A disadvantage for use is the intrinsically high viscosity which is characteristic of these random copolymer structures.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

Recognizing the disadvantages explained, it is an object of this invention to find novel copolymers based on polysiloxanes with amino and/or quaternary ammonium groups, which, coupled with good synthetic accessibility, enable a multitude of structures which can be determined in a controlled manner and hence also profiles of properties which can be adjusted over a wide range.

In a departure from the principle of randomness accepted in the teaching of WO 02/092904, the formation of clearly sequenced copolymer structures, which comprise aminic or ammonium functions, siloxane segments and polyoxyalkylene segments, shall be enabled. The principle of formation of the copolymers shall additionally give the option of freely selecting the content of incorporated nitrogen within certain limits.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The object of the invention is achieved by novel linear polydimethylsiloxane-polymer copolymers.

The invention therefore provides novel linear polydimethylsiloxane-polyether copolymers with amino and/or quaternary ammonium groups, which are obtainable by the reaction of organopolysiloxanes functionalized with secondary aminoalkyl groups with the reaction products formed from compounds containing epoxy groups and amines.

The affinity for the textile and/or fibrous carrier and ultimately, as a result of this, the substantivity of the copolymer structure claimed in accordance with the invention thereon is determined by the defined distance of the nitrogen functions which enter into electrostatic interaction from the surface of the substrate. In other words, the synthesis route claimed in accordance with the invention leads to structurally balanced softener additives which have neither an undesired accumulation of siloxane functions nor of amino organic functions. As a result, the process claimed here for preparation and the copolymer which results therefrom differ from the copolymer compositions according to the teaching of WO 02/092904, which can even contain, as a consideration of the extreme case, purely organosilicone (A(amine)A) and purely organic (B(amine)B) compounds. The presence of these compounds characterized by diametrically opposed polarity causes undesired turbidity and separation phenomena.

More particularly, the method indicated in U.S. Pat. No. 5,486,634 for preparing the organopolysiloxanes functionalized with secondary aminoalkyl groups is found to be a favourable route for these reactants.

The invention therefore further provides a process for preparing the inventive copolymers.

The preparation of the inventive copolymers proceeds stepwise and is characterized in that a) a diepoxide is first reacted with at least one amine compound to give a chain-extended adduct bearing a terminal glycidyl group, the molar ratio of diepoxide to amine being variable but at least greater than 1:1, and b) this intermediate is then reacted with a linear polysiloxane bearing a terminal secondary amino group, c) optionally, the nitrogen atoms can be completely or partially quaternized at any point in this process by adding acids or alkylating reagents, and d) also optionally, water or organic compounds selected from the group of the polyethers, polyols or alcohols can be added as diluents, emulsifiers or modifiers.

The epoxy components used in this process according to the invention are preferably diepoxides or diglycidyl ethers of the formula (1)

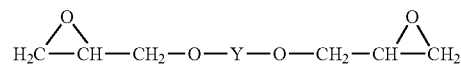

Formula (1)

where

Y is any divalent organic radical, preferably a divalent hydrocarbon radical which may be interrupted by oxygen atoms. More particularly, Y is a divalent polyether radical of the —(CH$_2$—CHR$^2$—O)$_m$—CH$_2$—CHR$^2$— type, where m is an integer from 0 to 50 and R$^2$ is hydrogen or an alkyl group having 1-4 carbon atoms.

Particularly suitable are diglycidyl ethers of polypropylene glycols and polyethylene glycols, as obtainable, for example, from DOW (D.E.R® 732, D.E.R® 736) and DOW Epoxy Systems (Polypox® R19—all trade marks mentioned are marks of the Dow Chemical Corp.). It is also possible to use different diepoxides of the formula (1) in a mixture.

Suitable reaction partners for such diglycidyl ethers are in principle all amine compounds with two reactive hydrogen atoms bonded to the nitrogen. Preference is given to using di-secondary amines of the formula (2)

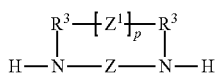 Formula (2)

where
R³ is independently a linear or branched aliphatic hydrocarbon radical which may be interrupted by heteroatoms such as O and N, or which may in turn be substituted by N- or O-containing groups or is a cycloaliphatic radical; R³ is monovalent or divalent when p is 0, or divalent when p is 1; R³ is preferably a hydrocarbon radical, more preferably an alkyl or alkylene group having 1 to 18 carbon atoms, Z is a divalent linear or branched hydrocarbon radical which may be interrupted by heteroatoms such as O and N or may in turn be substituted by N- or O-containing groups; Z is preferably an alkylene group having 2 to 18 carbon atoms, Z¹ is independently a Z radical and p is either 0 or 1.

When R³ is divalent, formula (2) encompasses cyclic amines, the two nitrogen atoms being constituents of this heterocyclic fragment. This includes piperazine, which is used with preference. Suitable linear di-secondary amines are, for example, N,N'-dimethylhexamethylene-1,6-diamine and N,N'-dimethyltetramethylene-1,4-diamine.

When p is 1, formula (2) encompasses cyclic amines, the two nitrogen atoms being constituents of this heterocyclic fragment. This includes piperazine, which is used with preference. Suitable linear di-secondary amines are, for example, N,N'-dimethylhexamethylene-1,6-diamine and N,N'-dimethyltetramethylene-1,4-diamine.

In the context of the present invention, at least one diepoxide component of the formula (1) in a molar excess is reacted with at least one amine compound of the formula (2) to give a chain-extended adduct bearing terminal glycidyl groups. The molar ratio of diepoxide to amine is variable and is at least greater than 1:1 and is preferably 10:1 to 1.1:1 and especially 6:1 to 1.5:1. The smaller the diepoxide excess, the higher the value of index x in formula (6) and the chain length of the resulting adduct. The higher the diepoxide excess, the more unadducted diglycidyl compounds are present in the reaction mixture which forms. In each case, the reaction product is a mixture of adducts with a molar mass distribution. The reaction can be performed within the temperature range of 20-180° C., preferably at 50 to 120° C. It is most favourable to initially charge the quantitatively predominant component—usually the diepoxide—and to add the second component—generally the amine—with stirring and optionally cooling. It is possible, but usually unnecessary, to perform the reaction in a solvent. Should this be required, for example owing to high viscosity, suitable solvents are, for example, ethanol, propanol, isopropanol, butanol, THF, acetone, toluene, etc. When the reaction is performed under inert conditions, such as under nitrogen, light-coloured or else pale yellowish end products are obtained.

To prepare the inventive copolymers, linear polysiloxanes which have terminal secondary amine groups and are of the formula (3) are used

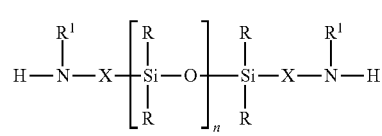 Formula (3)

where
R is an alkyl radical having 1-8 carbon atoms, preferably a methyl group,

R¹ is any hydrocarbon radical, preferably an alkyl radical having 1 to 20 carbon atoms, more preferably an alkyl radical having 1 to 4 carbon atoms, especially a methyl or ethyl group, X is a divalent linear or branched hydrocarbon radical which has 1-20 carbon atoms and may be interrupted by nitrogen atoms or aminic groups, and n is an integer from 1 to 500, preferably an integer from 5 to 300, more preferably an integer from 10 to 200.

Such polysiloxanes functionalized with terminal secondary amine groups are preparable, for example, by the route described in U.S. Pat. No. 5,486,634. Especially suitable in the context of the present invention are those amine-functional polysiloxanes which are obtainable by hydrosilylating N-ethylmethylallylamine onto α,ω-SiH-siloxanes. R¹ here corresponds to an ethyl group, X to the $CH_2$—$CH(CH_3)$—$CH_2$ fragment.

The reaction between at least one aminosiloxane of the formula (3) and at least one diepoxide-amine adduct is preferably accomplished in a solvent such as isopropanol, ethanol, propanol or THF, in order to compatibilize the two reactants. The stoichiometry is in principle as desired, but preference is given to reacting the two components in an approximately equimolar ratio. The relation of secondary amino groups from the siloxane of the formula (3) to the epoxy groups of the diepoxide-amine adduct is preferably 1.5:1 to 0.7:1, more preferably 1.3:1 to 0.9:1. According to which of the two reactants is possibly used in excess, copolymers with linear structures are formed with terminal epoxy or amine groups. To achieve more storage-stable products, it is advantageous to use the aminosiloxane in a slight excess relative to the diepoxide-amine adduct component. The reaction is accomplished at temperatures between 20° C. and 180° C., preferably at 60° C. to 120° C. It is possible either to initially charge the siloxane compound and to add the diepoxide-amine adduct, or to proceed in the reverse metering sequence. The solvent can remain in the product at the end or, if required, be removed by processes known to those skilled in the art, for example by distillation. Anywhere in the preparation process, most favourably after the end of the above-described reaction in the system still comprising solvent, it is optionally possible to add acids, preferably carboxylic acids such as formic acid, acetic acid, propionic acid, lactic acid, oxalic acid, citric acid or tartaric acid, aromatic carboxylic acids such as benzoic acid or salicylic acid, but equally also inorganic acids such as phosphoric acid, sulphuric acid, toluenesulphonic acid, methanesulphonic acid or hydrochloric acid, which forms quaternary ammonium groups. The amount of the acid used, based on nitrogen, is variable and is preferably between 0.01 mol and 2 mol, preferably 0.1 to 1.5 mol, per nitrogen atom.

In the context of the inventive teaching, it is likewise possible to isolate the non-neutralized copolymer and then, as detailed above, to neutralize it or undertake a quaternization of the amino groups. In the quaternization of the amine functions, alkylating reagents such as alkyl halides or alkyl sulphates (e.g. dimethyl sulphate) are typically used. Accompanying the quaternization, the copolymer, compared to the unmodified aminic precursor or salts thereof, gains substantivity on textile or fibrous substrates and also influence on the tendency thereof to become electrostatically charged.

The process according to the invention allows, in a simple manner, formation of strictly linear copolymer structures in which siloxane units and amine-functional organic sequences are present in strictly regularly alternating sequence. The hydrophobic siloxane character can be adjusted almost as desired through the siloxane chain length, and the hydrophilic character and the amine content through the selection of the diepoxide-amine stoichiometry in the precursor. Thus, it is possible to reproducibly produce structures which are exactly defined in terms of sequence of the repeat units in the copolymer chain.

The invention therefore provides a process for preparing novel linear copolymer structures consisting of alternating polysiloxane blocks and amino organic blocks, the nitrogen atoms of which are optionally in the form of quaternary ammonium groups, in which a) a diglycidyl ether of the formula (1) is first reacted in a molar excess with at least one amine compound of the formula (2) to give a chain-extended adduct bearing terminal glycidyl groups, the molar ratio of diepoxide to amine being variable and preferably being 10:1 to 1.1:1, and b) this intermediate is subsequently reacted with a linear polysiloxane which bears terminal secondary amino groups and is of the formula (3), preferably in a molar ratio of 1.5:1 to 0.7:1 and optionally in a solvent, c) optionally, the nitrogen atoms can be completely or partly quaternized anywhere in this process, most favourably after the end of the above-described reaction in the system still comprising solvent, optionally by adding acids such as preferably carboxylic acids, but also inorganic acids or alkylating reagents, such as alkyl halides or alkyl sulphates, and d) likewise optionally, water or organic compounds such as polyethers, polyols or alcohols are added as diluents, emulsifiers or modifiers.

The copolymers prepared in accordance with the invention are thus compounds of the general formula (4)

H-A—[(B—C)$_x$—B-A]$_y$—H  Formula (4)

where

A is a siloxane fragment from the structure of the aminosiloxane of the formula (3) according to formula (5)

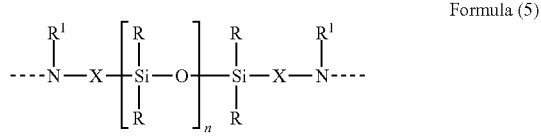

Formula (5)

B is an organic fragment which arises from the epoxy ring opening of the diglycidyl ether of the formula (1) according to formula (6)

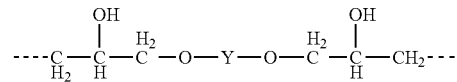

Formula (6)

C is a fragment from the amine structure of the formula (2) according to formula (7)

Formula (7)

and where the X, Y, Z, $Z^1$, $R^1$, $R^2$ and $R^3$ radicals and the n, m and p indices are each as defined above, x is from 0.1 to 10, preferably 0.2 to 5, y is from 1.1 to 50, preferably 1.2 to 30.

Formula (4) illustrates not only the strict block sequence of the repeat units A, B and C defined by the preparation process according to the invention, but also the attachment of the siloxane body to the amino organic block exclusively via an amine group of the —X—N($R^1$)— type, which clearly distinguishes the inventive copolymers from the non-(AB)n structures in WO 02/092904.

The indices represented in the formulae shown here and the value ranges of the indices reported should be interpreted as the mean values of the possible statistical distribution of the structures actually present and/or mixtures thereof. This is also true of those structural formulae shown in exact form per se.

The invention further provides the copolymers of the formula (4) preparable by the process presented, and the derivatives thereof which bear ammonium groups and have been quaternized with acids and/or alkylating agents.

It is familiar to the person skilled in the art that the compounds are present in the form of a mixture with a distribution of the indices mentioned regulated essentially by statistical laws.

Depending on the siloxane structure and the chain length thereof, the polysiloxanes with amino or quaternary ammonium groups are not self-emulsifiable or soluble in water. They can be introduced into an aqueous formulation through additions of emulsifiers and/or solvents. The emulsifiers used are typically fatty alcohol ethoxylates with degrees of ethoxylation between 3 and 12, specifically in a ratio of copolymer to the fatty alcohol ethoxylate of 5:1 to 1:1. It is equally possible for solvents to be used, for example high-boiling glycols such as dipropylene glycol or butyldiglycol.

The invention therefore further provides compositions which comprise the inventive copolymers, especially concentrates, compounds/emulsion concentrates and/or aqueous formulations, aqueous emulsions and/or solutions thereof, a formulation or emulsion in organic compounds such as polyethers, polyols, alcohols.

The invention further provides for the use of the inventive compounds, obtainable by the process according to the invention, as non-permanent or permanent softeners for fabrics selected, for example, from the group comprising wovens, textile wovens, knits, nonwovens, tissue (paper fibre) and/or fibres of natural and/or synthetic raw materials and/or leather and/or hair and/or hide, in which case the softener can optionally also impart hydrophilic properties to the fabrics treated therewith. More particularly, the inventive compounds impart hydrophilic properties with simultaneous achievement of a good hand and good permanence.

It is a further object of the invention to provide compounds and formulations comprising these compounds, which are capable both of improving properties such as combability, softness, volume, shapeability, manageability, disentangleability of undamaged and damaged hair, and/or else of imparting an appealing shine to the hair. The compounds should thus exhibit an improved or at least equally good individual effect, but overall an improved combined effect of mechanical and other properties.

This invention further provides for the use of the copolymers of the general formula (4) or of the mixtures comprising these compounds in shine-improving cosmetic formulations, as hair treatment compositions and hair aftertreatment compositions to be rinsed out of or to remain in the hair, for example in shampoos with or without marked conditioning action, conditioners, 2 in 1 shampoos, rinses, hair repair treatments, hair masks, styling aids, styling compositions, hair drying lotions, hair-setting compositions, permanent wave compositions, hair smoothing compositions and/or compositions for dyeing the hair.

A further advantage of the inventive use is that the polysiloxanes with quaternary functions of the formula (4) can exert outstanding conditioning effects on the skin. This conditioning effect on the skin can prevent a dry, brittle or rough state of the skin after uses of a cosmetic aqueous surfactant formulation, and achieve a pleasant, silky-smooth skinfeel.

The present invention further provides cosmetic, dermatological and pharmaceutical formulations and cosmetic personal care and body/skin cleaning compositions which are obtained by the use of the inventive copolymers and comprise, for example, at least one additional component selected from the group comprising emollients, emulsifiers and surfactants, thickeners/viscosity regulators/stabilizers, UV light protection filters, antioxidants, hydrotropes (or polyols), solids and fillers, film formers, pearlescent additives, active deodorant and antiperspirant ingredients, insect repellents, self-tanning agents, preservatives, conditioners, perfumes, dyes, active cosmetic ingredients, care additives, superfatting agents, solvents. Substances which can be used as illustrative representatives of the individual groups are known to those skilled in the art and can be taken, for example, from German Application DE 102008001788.4. This patent application is hereby incorporated by reference and is therefore considered to be part of the disclosure.

The process according to the invention permits, through the control of block structures of very different sequence length, the siloxane content in relation to the organic component and to the number of the optionally quaternized nitrogen atoms to be tailored within wide limits flexibly to the desired field of application. For example, copolymers with a high silicone content give rise to a pleasant hand of the woven fabric treated therewith, and they simultaneously have a relatively low viscosity which allows such compounds to be formulated in aqueous form.

More particularly, the inventive linear organomodified polysiloxanes impart a very good hydrophilic softness to woven textile fabrics, and possess an increased permanence on textiles. Furthermore, high rebound elasticity and improved crease recovery of a fabric thus finished are to be considered as further positive properties.

The inventive copolymers can be used and optionally applied, for example, as softeners for textiles and woven fabrics in the form of concentrates, compounds/emulsion concentrates, formulations and liquors produced therefrom, the copolymers being used in such systems in proportions of 0.5 to 99% by weight, preferably of 3 to 70% by weight, in particular of 5 to 50% by weight, based on the overall formulation.

"Liquor" represents a usually aqueous liquid in which textiles are washed, bleached, dyed or impregnated. The term "liquor" means the entirety of solvent (usually water) and all constituents present (dissolved, emulsified or dispersed) therein, for example dyes, emulsifiers and further assistants. The entirety of the constituents dissolved in the liquor is commonly also referred to as the solids content, the solids content specifying the drying residue after evaporation of the volatile constituents (at about 100° C.-105° C.). The amount of the components of a liquor is usually reported in g/l for liquids or % (based on the fabric weight).

In the textile sector, a treatment liquor is quite generally referred to as the bath (usually aqueous) in which (or with which) the woven fabric is finished with one or more (surface-active) substances. In addition to the main systems, there are further application forms such as spray application, knife-coating or roller application, according to the end use and hence viscosity of the product.

For aqueous systems, principally two systems are used:

For substantive, i.e. cationic, products—exhaustion processes: here, in principle like the fabric softener in a washing machine, the woven fabric is agitated in the liquor at a particular temperature for a particular time. Subsequently, the liquor is discharged and the woven fabric is dried.

For nonsubstantive and substantive products—padding application, for example with a Mat this HVF laboratory padder; here, the woven fabric is passed through the liquor and squeezed between the rollers (by the mangle principle) to a residual moisture content and then dried.

The invention therefore further provides a concentrate, a compound/emulsion concentrate, a formulation or an emulsion according to the definitions which follow.

Concentrate refers to the virtually pure copolymer compound of the formula (4) with a content of about 90-100% by weight, which is admixed with only minor proportions of solvents—these are generally not soluble in water and not self-emulsifiable either.

Compounds or emulsion concentrates contain 50-90% by weight, preferably 50-80% by weight, of the copolymer compound and, as further constituents, water and/or solvents selected from the group of the glycols, unbranched and/or branched alcohols and/or alkyl ethers having 1 to 6 carbon atoms and optionally one or more nonionic emulsifiers, for example an alcohol ethoxylate having 3-25 ethylene oxide units. Compounds and emulsion concentrates are generally water-soluble or self-emulsifiable.

Formulations and/or (aqueous) emulsions contain 5-20% by weight of the inventive copolymer, solvents, emulsifiers (including cationic or amphoteric emulsifiers), water. The solids content of these formulations or emulsions is generally about 40% by weight.

The aforementioned concentrates, compounds and/or formulations/emulsions are used, by dilution in water, to produce the (application) liquors (application/finishing baths) at the manufacturing premises/finishing premises. Typical liquor concentrations in the case of padding application are, for example, 5-80 g of formulation/emulsion per liter of liquor solution or application liquor.

The inventive copolymers can be used in haircare systems in combination with other active ingredients and assistants. According to the end use, such compositions are those comprising 2 to 25% by weight of one or more wash-active surfactants from the group of the anionic, nonionic, amphoteric or zwitterionic surfactants, 0.5 to 10% by weight of one or more emulsifiers, 0.5 to 10% by weight of one or more bodying agents, 0.5 to 10% by weight of one or more, preferably cationic, surfactants or emulsifiers, 0.5 to 20% by weight of one or more cosmetic oils, silicone oils or emollients, and customary assistants and additives in customary concentrations, and additionally comprising one or more active hair cosmetics ingredients selected from the group of the cationic polymers, for example quaternized cellulose and derivatives thereof, chitosan and derivatives thereof, cationic alkylglycosides, cationic guar derivatives, polymers of dimethyldiallylammonium salts and copolymers thereof with esters and amides of acrylic acid and methacrylic acid, copolymers of vinylpyrrolidone with quaternized derivatives of dialkylaminoalkyl acrylate and methacrylate, for example diethyl sulphate-quaternized vinylpyrrolidone-dimethylaminoethyl methacrylate copolymers, vinylpyrrolidone-vinylimidazolium methochloride copolymers, terpolymers of the vinylpyrrolidone, caprolactam and acrylamide monomers, quaternized polyvinyl alcohol and those polymers known by the INCI designations Polyquaternium-2, Polyquaternium-17, Polyquaternium-18, Polyquaternium-27 and Polyquaternium-37, cationic or nonionic protein hydrolysates of vegetable or animal origin based on keratin, collagen, elastin, wheat, rice, soy, milk, silk, maize or further silicone derivatives, for example Dimethiconol or Dimethicone (INCI designations for polydimethylsiloxanes) and modified silicones which may be terminally functionalized (INCI prefix Bis-) and/or graft-functionalized, namely, for example, alkoxysilicones and alkylsilicones with long-chain alkyl groups, polyoxyalkyl-modified silicones such as PEG/PPG-3/10 Dimethicone or Bis-PEG/PPG-20/20 Dimethicone with or without alkyl ether group and esters thereof, for example Dimethicone PEG-7 Cocoate and polyfunctionalized silicones, for example Cetyl PEG/PPG-10/1 Dimethicone or Methyleugenyl PEG-8 Dimethicone, and additionally silicone copolymers with acrylates, including those copolymers with and without alkyl modification, branched silicone derivatives such as Dimethicone/Silsesquioxane Copolymer, crosslinked silicone copolymers such as Dimethicone Crosspolymer, Alkyl Dimethicone/Divinyldimethicone Crosspolymer, Cetearyl Dimethicone Crosspolymer or Cetearyl Dimethicone/Vinyl Dimethicone Crosspolymer, amino-functionalized silicones such as Amodimethicone, Aminopropyl Dimethicone, PEG-7 Amodimethicone, Methoxy PEG/PPG-7/3 Aminopropyl Dimethicone or ionically modified silicones such as Dimethicone Propyl PG-Betaine, vitamins, panthenol, pyrrolidonecarboxylic acid, bisabolol, plant extracts, creatine, ceramides and UV absorbents.

Further configurations and subjects of the invention are evident from the claims, the disclosure-content of which is fully incorporated into this description.

The inventive copolymers with amino and/or quaternary ammonium groups and the process for preparation thereof are described by way of example hereinafter, without intention that the invention be restricted to these illustrated embodiments.

When ranges, general formulae or compound classes are specified below, these shall encompass not only the corresponding ranges or groups of compounds mentioned explicitly, but also all sub-regions and sub-groups of compounds which can be obtained by selecting individual values (ranges) or compounds.

Experimental Section

For the inventive preparation of the copolymers, the following linear aminosiloxanes were used, which were obtained by the process described in U.S. Pat. No. 5,486,634, by hydrosilylating the corresponding α,ω-SiH-polydimethylsiloxanes with N-ethylmethylallylamine:

| Aminosiloxane 1 | Aminosiloxane 2 | Aminosiloxane 3 |
| --- | --- | --- |
| Mean molar mass 6100 g/mol approx. 80 dimethylsiloxy units in the polymer chain | Mean molar mass 3900 g/mol approx. 50 dimethylsiloxy units in the polymer chain | Mean molar mass 2400 g/mol approx. 30 dimethylsiloxy units in the polymer chain |

The diepoxide used was a polypropylene glycol diglycidyl ether from DOW Epoxy Systems (Polypox® R19) with an epoxide equivalent weight of 329 g/mol and an epoxide number of 171 mg KOH/g.

The viscosities were measured on the basis of DIN 53019 with a Brookfield (model LVT) rotational viscometer at 25° C.

Determination of the Siloxane Quat Nitrogen Content:

The quaternary nitrogen is determined by means of potentiometric titration with a dodecylsulphate solution as the titrant using an electrode combination consisting of a special solvent-resistant sensor electrode, for example the Surfactrode Resistant (Metrohm AG), and a reference electrode (Ag/AgCl cartridge double junction, Metrohm AG). The sample to be determined for quat nitrogen is weighed into a titration beaker with an accuracy of 0.1 mg. After dilution in 10 ml of MIBK, 10 ml of denatured ethanol and 0.2 ml of TEGO® add (from Metrohm AG Art. No. 6.2317.100) are pipetted in, then 10 ml of pH 10 buffer solution are added and the mixture is diluted with 80 ml of dist. water. This is followed by titration on a titroprocessor against 0.005 molar sodium dodecylsulphate solution. Taking account of the consumption of this titer solution and the weight, the content of quaternary nitrogen is determined.

Preparation of the Diepoxide-Diamine Adducts:

Adduct 1:

A glass flask is initially charged with 400 g of the Polypox® R19 diepoxide which are heated to 80° C. with nitrogen inertization. 25.6 g of a piperazine (68% in water) molten at approx. 50° C. are added in portions while stirring and cooling within 1 h. Continued reaction for 2 h forms a yellowish, clear reaction product (viscosity at 25° C.: 1020 mPas).

Adduct 2:

A glass flask is initially charged with 400 g of the Polypox® R19 diepoxide which are heated to 80° C. with nitrogen inertization. 30.4 g of a piperazine (68% in water) molten at approx. 50° C. are added in portions while stirring and cooling within 1 h. Continued reaction for 2 h forms a yellowish, clear reaction product (viscosity at 25° C.: 1100 mPas).

Adduct 3:

A glass flask is initially charged with 400 g of the Polypox® R19 diepoxide which are heated to 80° C. with nitrogen inertization. 38.0 g of a piperazine (68% in water) molten at approx. 50° C. are added in portions while stirring and cooling within 1 h. Continued reaction for 2 h forms a yellowish, clear reaction product (viscosity at 25° C.: 2870 mPas).

Preparation of the Inventive Copolymers:

Copolymer 1:

2500 g aminosiloxane 1 and 2500 g of isopropanol are initially charged in a glass flask equipped with a reflux condenser and heated to 80° C. with nitrogen blanketing. 383.8 g of adduct 1 are added while stirring within 45 min. After continued reaction at 80-82° C. (reflux) for 2 h, the reflux condenser is exchanged for a distillation system, and isopropanol is removed by distillation at bottom temperatures up to 110° C. and vacuum of not less than 20 mbar. After decompressing with nitrogen and cooling to <80° C., 16.7 g of acetic acid are added while stirring. After 20 min of stirring time, the clear yellowish product is discharged (viscosity at 25° C.: 8500 mPas). The siloxane quat nitrogen content determined by titrimetry corresponds to theory.

Copolymer 2:

250 g of aminosiloxane 2 and 250 g of isopropanol are initially charged in a glass flask equipped with a reflux condenser and heated to 80° C. with nitrogen inertization. 67.2 g of adduct 2 are added while stirring within 45 min. After continued reaction at 80-82° C. (reflux) for 2 h, the reflux condenser is exchanged for a distillation system, and isopropanol is removed by distillation at bottom temperatures up to 110° C. and vacuum of not less than 20 mbar. After decompressing with nitrogen and cooling to <80° C., 1.8 g of acetic acid are added while stirring. After 20 min of stirring time, the slightly turbid yellowish product is discharged (viscosity at 25° C.: 5150 mPas). The siloxane quat nitrogen content determined by titrimetry corresponds to theory.

Copolymer 3:

250 g of aminosiloxane 1 and 250 g of isopropanol are initially charged in a glass flask equipped with a reflux condenser and heated to 80° C. with nitrogen inertization. 52.2 g of adduct 3 are added while stirring within 45 min. After continued reaction at 80-82° C. (reflux) for 2 h, the reflux condenser is exchanged for a distillation system, and isopropanol is removed by distillation at bottom temperatures up to 110° C. and vacuum of not less than 20 mbar. After decompressing with nitrogen and cooling to <80° C., 1.8 g of acetic acid are added while stirring. After 20 min of stirring time, the slightly turbid yellowish product is discharged (viscosity at 25° C.: approx. 10 500 mPas). The siloxane quat nitrogen content determined by titrimetry corresponds to theory.

Copolymer 4:

250 g of aminosiloxane 3 and 250 g of isopropanol are initially charged in a glass flask equipped with a reflux condenser and heated to 80° C. with nitrogen inertization. 97.5 g of adduct 1 are added while stirring within 45 min. After continued reaction at 80-82° C. (reflux) for 2 h, the reflux condenser is exchanged for a distillation system, and isopropanol is removed by distillation at bottom temperatures up to 110° C. and vacuum of not less than 20 mbar. After decompressing with nitrogen and cooling to <80° C., 2.3 g of acetic acid are added while stirring. After 20 min of stirring time, the clear yellowish product is discharged (viscosity at 25° C.: 4200 mPas). The siloxane quat nitrogen content determined by titrimetry corresponds to theory.

Copolymer 5:

150 g of aminosiloxane 1 and 150 g of isopropanol are initially charged in a glass flask equipped with a reflux condenser and heated to 80° C. with nitrogen blanketing. 23.0 g of adduct 1 are added while stirring within 10 min. After continued reaction at 80-82° C. (reflux) for 2.45 h, the reflux condenser is exchanged for a distillation system, and isopropanol is removed by distillation at bottom temperatures up to 110° C. and vacuum of not less than 20 mbar. After decompressing with nitrogen and cooling to <80° C., 1.6 g of acetic acid are added while stirring. After 20 min of stirring time, the clear yellowish product is discharged (viscosity at 25° C.: 9000 mPas). The siloxane quat nitrogen content determined by titrimetry corresponds to theory.

Copolymer 6:

150 g of aminosiloxane 1 and 150 g of isopropanol are initially charged in a glass flask equipped with a reflux condenser and heated to 80° C. with nitrogen blanketing. 25.0 g of adduct 1 are added while stirring within 15 min. After continued reaction at 80-82° C. (reflux) for 2 h, the reflux condenser is exchanged for a distillation system, and isopropanol is removed by distillation at bottom temperatures up to 110° C. and vacuum of not less than 20 mbar. After decompressing with nitrogen and cooling to <80° C., 1.0 g of acetic acid are added while stirring. After 20 min of stirring time, the yellowish opaque product is discharged. The siloxane quat nitrogen content determined by titrimetry corresponds to theory.

Use Examples

General Formulation 5-50% by weight of the aminosiloxane are initially charged in a beaker with propeller stirrer while stirring. Subsequently, in this order, 5-25% by weight of dipropylene glycol or butyldiglycol, 3-15% by weight of a fatty alcohol ethoxylate with a degree of ethoxylation of 6, are added while stirring. Finally, the mixture is made up to 100% by weight with water.

Formulation 1—Inventive:

20 parts by weight of the inventive copolymer 1 with quaternary ammonium groups from example 1 are initially charged in a beaker with propeller stirrer while stirring. Subsequently, in this order, 10 parts of dipropylene glycol, 10 parts of a fatty alcohol ethoxylate with a degree of ethoxylation of 6, are added while stirring. Finally, the mixture is made up with 60 parts of water. This gives a clear low-viscosity formulation.

Formulation 2—Inventive:

Analogously to the preparation of formulation 1, formulation 2 was prepared from the inventive copolymer 5.

Formulation 3—Noninventive:

An emulsion according to formulation 1 was prepared with a commercial Siliconquat, Tegopren® 6924. Tegopren® 6924 is a linear siloxane with terminal modification by quat functions.

Formulation 4—Noninventive:

An emulsion of a commercial aminosiloxane (e.g. Biosoft from BioTex) was prepared with an active content of 20% by weight.

Formulation 5—Inventive:

Analogously to the preparation of formulation 1, formulation 5 was prepared from the inventive copolymer 6.

Formulation 6—Noninventive:

Tegopren® 7100, a commercial emulsion of a siloxane with pendant modification, the modification comprising polyether and amino functions alongside one another, was prepared with an active content of 20% by weight.

Application Examples

To test the hand achievable when the aminosiloxanes are used (tactile assessment) and also the achievable hydrophilicity, products consisting of native fibres were finished therewith by the following method:

Padding Method:

To examine the softness of the particular emulsions, knit cotton fabric (160 g/m$^2$) and terry cotton fabric (400 g/m$^2$) were padded with a liquor which contained in each case 20 g/l of the corresponding emulsion, then the textiles were squeezed down to a liquor pickup of approx. 100% by weight and dried at a temperature of 130° C. for three minutes.

To examine the hydrophilicity, woven cotton fabric (200 g/m$^2$) was padded with a liquor which contained in each case 30 g/l of the corresponding emulsion, and then squeezed off to a liquor pickup of approx. 100% by weight and dried at 130° C. for three minutes.

Test Methods:

Hand Assessment:

To assess the fabric hand, an experienced team was put together, which assessed the anonymized hand samples, the knit and terry fabrics finished with the emulsions, with the aid of a hand panel test. The hand samples of knit fabric were additionally supplemented with an inconspicuously labelled untreated sample.

Testing of Hydrophilicity:

To test the hydrophilicity, the test method based on DIN 53924 for measuring the height of rise of water was used. This involved cutting each finished cotton test fabric into five strips of length 25 cm and width 1.5 cm, marking the sides with a water-soluble pen and securing it to a holder in a taut perpendicular position, but without tension. The holder is subsequently placed into a water bath for 5 minutes such that 2 cm of the strips are immersed into the water. The water-soluble marking serves for better discernibility of the height of rise by the running of the ink when wetted with water. Once the holder has stood outside the water bath for 10 minutes, the height of rise in cm is read off and determined against the blank values (height of rise for the untreated cotton strips× cm=100%) and reported in % of the blank value.

Washing Operation:

The washing operations were conducted in a commercial Miele Novotronic W 918 washing machine, with colour wash without prewash at 40° C., using IECA Base standard WFK laundry detergent and 3 kg of cotton ballast fabric. Finally, the woven fabric thus treated was dried at room temperature for 12 hours.

The test results for softness are shown in Tables 1 to 3, and those for hydrophilicity in Table 4.

TABLE 1

Assessment of softness on knit cotton fabric after padding application

| | |
|---|---|
| Formulation 1 Inventive | +++ |
| Formulation 2 Inventive | ++ |
| Formulation 3 noninventive | +++ |
| Formulation 4 noninventive | +++ |
| Untreated | − |

+++ excellent,
++ very good,
+ good,
o satisfactory,
− poor

TABLE 2

Assessment of softness on terry cotton fabric after padding application

| | |
|---|---|
| Formulation 1 inventive | ++ |
| Formulation 2 inventive | +++ |
| Formulation 3 noninventive | ++ |
| Formulation 4 noninventive | ++ |
| Untreated | − |

+++ excellent,
++ very good,
+ good,
o satisfactory,
− poor

TABLE 3

Assessment of softness on knit cotton fabric after padding application

| | Before the wash | After the 1st wash | After the 3rd wash | After the 5th wash |
|---|---|---|---|---|
| Formulation 3 noninventive | ++ | ++ | o | o |
| Formulation 4 noninventive | +++ | +++ | +++ | ++ |
| Formulation 5 inventive | +++ | +++ | ++ | + |
| Formulation 6 noninventive | + | o | − | − |
| Untreated | o | − | − | − |

+++ excellent,
++ very good,
+ good,
o satisfactory,
− poor

TABLE 4

Assessment of water pickup of woven cotton fabric after padding application

| Woven fabric type of the treated cotton | Height of rise in % of the blank value |
|---|---|
| Formulation 1—inventive | 84.3 |
| Formulation 2—inventive | 82.6 |
| Formulation 3—noninventive | 84.1 |
| Formulation 4—noninventive | 30.3 |
| Formulation 5—inventive | 81.9 |
| Formulation 6—noninventive | 90.5 |
| Untreated | 100.0 |

The results in Table 4 show an excellent water pickup of the woven cotton fabrics treated with the inventive formulations of more than 80% of the height of rise of the untreated sample. The increased hydrophilicity of the inventive formulations is thus demonstrated, especially compared to the noninventive formulation 4. At the same time, the textile fabrics treated with the inventive formulations exhibit excellent softness combined with very good permanence (formulation 5 in Table 3). Excellent softness combined with good permanence can also be achieved with the noninventive formulation 4, but this exhibits exceptionally hydrophobic and hence undesired behaviour with regard to water pickup.

Table 4 additionally shows that the results for the noninventive formulations 3 and especially 6 with regard to water pickup are similar to those according to the invention, but the softness of knit cotton fabric is significantly poorer for these formulations, as can be inferred from Table 3.

Explanation:

The result is a soft, very fleecy and silky hand of the textile fabrics finished with the inventive products (formulations 1, 2 and 5), which is essentially maintained even after repeated washing (formulation 5). The inventive products exhibit excellent hand coupled with simultaneously excellent hydrophilicity compared to commercial products.

Formulation 5 additionally shows, on smooth woven fabric (knit cotton fabric), a significantly improved permanence over 5 washes, which is reflected in a virtually constant good assessment of hand.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A linear polydimethylsiloxane-polyether copolymer with an amino group and/or a quaternary ammonium group, obtained by:
    reacting an organopolysiloxane functionalized with a secondary aminoalkyl group with a reaction product formed from compounds containing epoxy groups and amines;
    wherein the linear polydimethylsiloxane-polyether copolymer is of the formula (4):

H-A-[(B—C)$_x$—B-A]$_y$-H    Formula (4);

where A is a siloxane fragment according to formula (5);

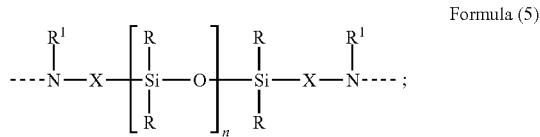

Formula (5)

where B is an organic fragment according to formula (6):

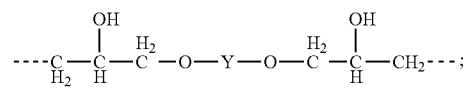

Formula (6)

where C is a fragment according to formula (7):

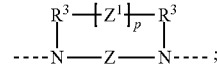

Formula (7)

where R is an alkyl radical having 1-8 carbon atoms;
where $R^1$ is any hydrocarbon radical;
where $R^3$ is a divalent methyl radical;
where X is a divalent linear or branched hydrocarbon radical which has 1-20 carbon atoms and may be interrupted by nitrogen atoms or aminic groups;
where Y is a divalent polyether radical of the formula:
    —(CH$_2$—CHR$^2$—O)$_m$—CH$_2$—CHR$^3$—;
    where m is an integer from 0 to 50; and
    where $R^2$ is hydrogen or an alkyl group having 1-4 carbon atoms;
where Z is a divalent ethyl radical;
where $Z^1$ is independently a Z radical;
where n is an integer from 1 to 500;
where p is 0;
where x is from 0.1 to 10; and
where y is from 1.1 to 50.

2. The linear polydimethylsiloxane-polyether copolymer according to claim 1;
    wherein the linear polydimethylsiloxane-polyether copolymer has been quaternized with acids and/or allylating agents and bears an ammonium group.

* * * * *